United States Patent
Kokal et al.

(10) Patent No.: US 11,105,722 B2
(45) Date of Patent: Aug. 31, 2021

(54) SCREENING DEMULSIFIERS FOR CRUDE LIVE OIL-WATER EMULSIONS

(71) Applicant: Saudi Arabian Oil Company, Dhahran (SA)

(72) Inventors: Sunil Kokal, Dhahran (SA); Zuhair Al-Yousif, Saihat (SA)

(73) Assignee: Saudi Arabian Oil Company, Dhahran (SA)

( * ) Notice: Subject to any disclaimer, the term of this patent is extended or adjusted under 35 U.S.C. 154(b) by 237 days.

(21) Appl. No.: 16/239,164

(22) Filed: Jan. 3, 2019

(65) Prior Publication Data
US 2020/0217768 A1    Jul. 9, 2020

(51) Int. Cl.
*G01N 13/00*    (2006.01)
*G01N 11/04*    (2006.01)
(Continued)

(52) U.S. Cl.
CPC ............. *G01N 13/00* (2013.01); *G01N 11/04* (2013.01); *G01N 33/2823* (2013.01);
(Continued)

(58) Field of Classification Search
CPC .... G01N 13/00; G01N 11/04; G01N 33/2823; G01N 21/85; G06K 9/00134; G06K 9/00147; G06K 9/6268; G06K 9/6293
See application file for complete search history.

(56) References Cited

U.S. PATENT DOCUMENTS

| 6,555,009 B2 | 4/2003 | Varadaraj |
| 2005/0087001 A1 | 4/2005 | Irani |

(Continued)

FOREIGN PATENT DOCUMENTS

| JP | 6160267 | 7/2017 |
| WO | WO 2004/053468 | 6/2004 |

(Continued)

OTHER PUBLICATIONS

International Search Report and Written Opinion issued in International Application No. PCT/US2019/067867 dated Apr. 7, 2020, 17 pages.

(Continued)

*Primary Examiner* — David Z Huang
(74) *Attorney, Agent, or Firm* — Fish & Richardson P.C.

(57) ABSTRACT

Certain implementations of the subject matter can be implemented to screen demulsifiers. A live emulsion of a live hydrocarbon sample and a water sample is flowed through a capillary viscometer. The live hydrocarbon sample includes dissolved gases retrieved from a hydrocarbon-carrying reservoir. While flowing the live emulsion through the capillary viscometer, a demulsifier sample is flowed through the capillary viscometer. The demulsifier sample is capable of causing breakdown of the live emulsion. Using the capillary viscometer, change in a viscosity of the live emulsion over time resulting from the breakdown of the live emulsion due to the demulsifier sample is measured. Multiple images of the breakdown of the live emulsion over time are captured. A strength of the live emulsion is classified based, in part, on the change in the viscosity of the live emulsion over time and on the plurality of images.

18 Claims, 4 Drawing Sheets

(51) Int. Cl.
    *G01N 33/28* (2006.01)
    *G06K 9/00* (2006.01)
    *G06K 9/62* (2006.01)
(52) U.S. Cl.
    CPC ..... *G06K 9/00134* (2013.01); *G06K 9/00147* (2013.01); *G06K 9/6268* (2013.01); *G06K 9/6293* (2013.01)

(56) References Cited

U.S. PATENT DOCUMENTS

| | | | | |
|---|---|---|---|---|
| 2011/0301061 | A1* | 12/2011 | McDaniel | C10G 33/08 506/12 |
| 2012/0127466 | A1 | 5/2012 | Karnes et al. | |
| 2012/0140058 | A1* | 6/2012 | McDaniel | B03C 11/00 348/86 |
| 2013/0026082 | A1* | 1/2013 | Al-Shafei | C10G 33/02 210/96.1 |

FOREIGN PATENT DOCUMENTS

| | | |
|---|---|---|
| WO | WO 2005/036181 | 4/2005 |
| WO | WO 2011/014202 | 2/2011 |
| WO | WO 2018/160068 | 9/2018 |

OTHER PUBLICATIONS

Abdulredha et al., "Overview on petroleum emulsions, formation, influence and demulsification treatment techniques," Arabian Journal of Chemistry, vol. 13, No. 1, Nov. 22, 2018, 26 pages.

Chen et al., "Demulsifying water-in-oil emulsions by ethyl cellulose demulsifiers studied using focused beam reflectance measurement," Chemical Engineering Science, vol. 130, Jul. 1, 2015, 10 pages.

He, "Destabilization and treatment of produced oil-water emulsions for EOR application using dissolved air flotation technique," in partial fulfillment of the requirements of the degree of Master of Science in Petroleum Engineering, May 2015, 127 pages.

Plasencia et al., "Pipe flow of water-in-crude oil emulsions: Effective viscosity, inversion point and droplet size distribution," Journal of Petroleum Science and Engineering, vol. 101, Jan. 1, 2013, 9 pages.

Zhang et al., "Hyperbranched poly(amido amine) demulsifiers with ethylenediamide/1,3-propanediamine as an initiator for oil-in-water emulsions with microdroplets," Fuel, IPC Science and Technology Press, vol. 226, Apr. 11, 2018, 8 pages.

International Search Report and Written Opinion issued in International Application No. PCT/US2019/067862 dated Mar. 31, 2020, 17 pages.

Xylem, "ViscoClock plus Automatische Viskositatsmessung Einfach Und Genau," Jul. 1, 2016, 2 pages.

Advincula, "Superhydrophobic Coatings and oil and Water Separation," Paper No. 9585, Nace International, Corrosion Conference and Expo, Mar. 26-30, 2017, 7 pages.

Alboudwarej et al., "Rheology of Heavy-Oil Emulsions," SPE 97886, presented at the 2005 SPE/PS-CIM/CHOA International Thermal Operations and Heavy Oil Symposium, SPE Production & Operations, Aug. 2007, 9 pages.

Allenson et al., "Application of Emulsion Viscosity Reducers to Lower Produced Fluid Viscosity," OTC 22443, Offshore Technology Conference, Oct. 4-6, 2011, 10 pages.

Alsabagh et al., "Demulsification of W/O emulsion at petroleum field and reservoir conditions using some demulsifiers based on polyethylene and propylene oxides," Egyptian Journal of Petroleum, vol. 25, Issue 4, Egyptian Petroleum Research Institute, Dec. 2016, 11 pages.

Al-Yaari et al., "Pressure drop reduction of stable water-in-oil emulsion flow: Role of water fraction and pipe diameter," IPTC 16883, presented at the International Petroleum Technology Conference, Mar. 26-28, 2013, 9 pages.

Arffin et al., "The rheology of light crude oil and water-in-oil emulsion," Procedia Engineering vol. 148, 4th International Conference on Process Engineering and Advanced Materials, Dec. 2016, 7 pages.

Kokal and Alvarez, "Reducing Pressure Drop in Offshore Pipelines by Controlling the Viscosities of Pressurized Emulsions," SPE 81511, presented at the SPE Middle East Oil Show, Apr. 5-8, 2003, 10 pages.

Kokal, "Chapter 12: Crude Oil Emulsions," Petroleum Engineering Handbook—vol. 1, Sep. 30, 2006, 38 pages.

Kumar et al., "Emulsion Flooding of Heavy Oil," SPE 129914, presented at the 2010 SPE Improved Oil Recovery Symposium, Apr. 24-28, 2010, 13 pages.

Tjoeng and Loro, "Viscosity Modelling of Pyrenees Crude Oil Emulsions," presented at the SPE Asia Pacific Oil and Gas Conference and Exhibition, Oct. 25-27, 2016, 18 pages.

Williams and Kokal, "Chapter 4: Fluid Sampling," Petroleum Engineering Handbook, vol. 1, Sep. 30, 2006, 44 pages.

Yi et al., "Research on crude oil demulsification using the combined method of ultrasound and chemical demulsifier," Journal of Chemistry, vol. 2017, Article IDS 9147926, Mar. 2017, 8 pages.

Zhao, "RPSEA Final Technical Report: Heavy viscous oil pressure, volume and temperature," 08121-2201-02, Research Partnership to Secure Energy for America (RPSEA), Feb. 4, 2015, 250 pages.

GCC Examination Report received in Gulf Cooperation Council Appln. No GC 2020-38949, dated Mar. 31, 2021, 4 pages.

* cited by examiner

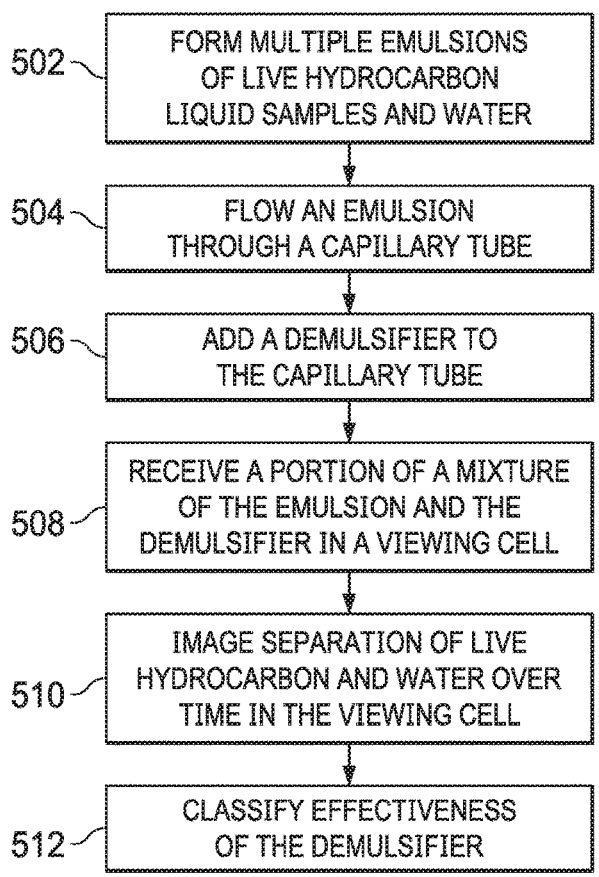
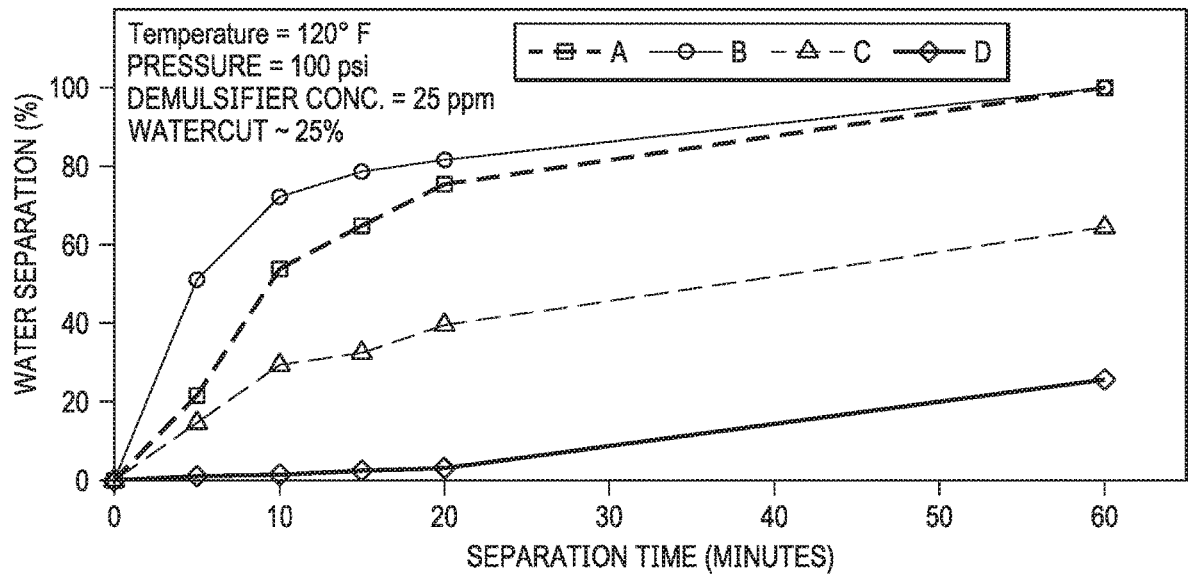

SCREENING DEMULSIFIERS FOR CRUDE LIVE OIL-WATER EMULSIONS

TECHNICAL FIELD

This disclosure relates to emulsions of hydrocarbon liquids and water and, more particularly, to analyzing effects of demulsifiers on emulsions of hydrocarbon liquids and water.

BACKGROUND

Hydrocarbons entrapped in subsurface reservoir rocks can be produced (that is, raised to the surface). Hydrocarbons are seldom produced alone; rather, they are often commingled with water which is also in the subsurface reservoir rocks. The produced water is generally present in the form of emulsions, which can present operational challenges during hydrocarbon production and processing, for example, in gas-oil separation plants (GOSPs). Untreated or improperly treated emulsions can result in issues such as occasional tripping of separation equipment in GOSPs, production of off-spec crude oil, increased pressure in flow lines, corrosion, and catalyst poisoning in downstream processing facilities, to name a few. To avoid these issues and to meet crude oil specifications for transportation, storage and export, emulsions have to be treated. Treating an emulsion can include mixing chemicals called demulsifiers to the emulsions to break or separate the emulsions.

SUMMARY

This disclosure describes techniques relating to evaluating effectiveness of demulsifiers to break hydrocarbon liquid-water emulsions. As used in this disclosure, live hydrocarbon is hydrocarbon containing dissolved gas in solution that may be released from solution at surface conditions. Dead hydrocarbon is hydrocarbon at sufficiently low pressure that it contains no dissolved gas. An emulsion is a dispersion (droplets) of one liquid in another immiscible liquid. The phase that is present in the form of droplets is the dispersed or internal phase, and the phase in which the droplets are suspended is called the continuous or external phase. For produced oilfield emulsions, one of the liquids is aqueous and the other is crude oil. As used in this disclosure, a live emulsion sample is a sample obtained from a surface processing facility, or a production stream, or subsurface reservoir rock that includes live hydrocarbons as the dispersed phase and water as the continuous phase.

Certain implementations of the subject matter can be implemented as a method. A live emulsion of a live hydrocarbon sample and a water sample is flowed through a capillary viscometer. The live hydrocarbon sample includes dissolved gases retrieved from a hydrocarbon-carrying reservoir. While flowing the live emulsion through the capillary viscometer, a demulsifier sample is flowed through the capillary viscometer. The demulsifier sample is capable of causing breakdown of the live emulsion. Using the capillary viscometer, change in a viscosity of the live emulsion over time resulting from the breakdown of the live emulsion due to the demulsifier sample is measured. Multiple images of the breakdown of the live emulsion over time are captured. A strength of the live emulsion is classified based, in part, on the change in the viscosity of the live emulsion over time and on the plurality of images.

Aspects of the disclosure combinable with any of the other aspects can include the following features. The demulsifier sample is a first demulsifier sample. The live emulsion is a first live emulsion. A second live emulsion of the hydrocarbon sample and the water sample is flowed through the capillary viscometer. While flowing the second live emulsion through the capillary viscometer, a second demulsifier sample is flowed through the capillary viscometer. Using the capillary viscometer, change in a viscosity of the second live emulsion over time resulting from the breakdown of the live emulsion due to the demulsifier sample is measured. Multiple images of the breakdown of the second live emulsion over time are captured.

Aspects of the disclosure combinable with any of the other aspects can include the following features. A concentration of the second demulsifier sample is different from a concentration of the first demulsifier sample.

Aspects of the disclosure combinable with any of the other aspects can include the following features. A temperature at which the second demulsifier sample and the second live emulsion are flowed is different from a temperature at which the first demulsifier sample and the first live emulsion are flowed.

Aspects of the disclosure combinable with any of the other aspects can include the following features. A pressure at which the second demulsifier sample and the second live emulsion are flowed is different from a pressure at which the first demulsifier sample and the first live emulsion are flowed.

Aspects of the disclosure combinable with any of the other aspects can include the following features. An image of the breakdown of the live emulsion over time includes bubbles indicative of the breakdown. The strength of the live emulsion is classified based on sizes and densities of the bubbles in the image.

Aspects of the disclosure combinable with any of the other aspects can include the following features. The live emulsion is formed by flowing the hydrocarbon sample and the water sample through the capillary viscometer, and applying a shear force to the hydrocarbon sample and the water sample in the capillary viscometer to form the live emulsion.

Aspects of the disclosure combinable with any of the other aspects can include the following features. A change in pressure across the capillary viscometer over time resulting from the breakdown of the live emulsion due to the demulsifier sample is measured. The strength of the live emulsion is classified based, in part, on the change in the pressure across the capillary viscometer over time.

Certain implementations of the subject matter can be implemented as a method. Multiple live emulsions are formed. Each live emulsion is formed from a live hydrocarbon sample and a water sample. Each live hydrocarbon sample includes dissolved gases retrieved from a hydrocarbon-carrying reservoir. Each live emulsion is flowed through a capillary viscometer. While flowing the live emulsion through the capillary viscometer, a demulsifier is injected into the capillary viscometer resulting in a breakdown of the live emulsion due to the demulsifier. Change in a viscosity of the live emulsion over time resulting from the breakdown of the live emulsion due to the demulsifier is measured. Change in a pressure across the capillary viscometer over time resulting from the breakdown of the live emulsion due to the demulsifier is measured. Multiple images of the breakdown of the live emulsion are captured over time. The multiple live emulsions are classified according to respective strengths of the live emulsion based, in part, on the change in the viscosity measured, the change in the pressure measured and the multiple images captured for each live emulsion.

Aspects of the disclosure combinable with any of the other aspects can include the following features. Each live emulsion is formed by flowing a mixture of the hydrocarbon sample and the water sample through the capillary viscometer until a viscosity of the mixture substantially stabilizes over time.

Certain implementations of the subject matter can be implemented as an apparatus including a viscometer and an imaging system. The viscometer is configured to flow at least one of a live emulsion formed from a live hydrocarbon sample, a water sample or a demulsifier sample configured to breakdown a live emulsion formed by the live hydrocarbon sample and the water sample. The live hydrocarbon sample includes dissolved gases retrieved from a hydrocarbon-carrying reservoir. The viscometer is configured to measure change in a viscosity of the live emulsion over time resulting from a breakdown of the live emulsion by the demulsifier sample. The imaging system is connected to the viscometer. The imaging system is configured to capture images or video of the breakdown of the live emulsion by the demulsifier sample.

Aspects of the disclosure combinable with any of the other aspects can include the following features. A first pump is fluidically connected to a first end of the viscometer. A second pump is fluidically connected to a second end, where the first and the second ends of the viscometer are opposing. The first pump and the second pump are configured to operate synchronously to flow the live emulsion and the demulsifier multiple times between the first end and the second end.

Aspects of the disclosure combinable with any of the other aspects can include the following features. The viscometer includes a differential pressure sensor connected to the viscometer. The differential pressure sensor is configured to sense a pressure differential across the viscometer due to the flow of the live emulsion of the demulsifier between the first end and the second end.

Aspects of the disclosure combinable with any of the other aspects can include the following features. An elongated tube is fluidically connected to the viscometer. The elongated tube can flow the live emulsion and the demulsifier sample. The elongated tube includes a transparent body.

Aspects of the disclosure combinable with any of the other aspects can include the following features. The apparatus includes a viewing cell within which the elongated tube is positioned. The viewing cell and the imaging system are spatially positioned such that the imaging system is configured to capture the images or the video when the live emulsion and the demulsifier sample flow through the elongated tube.

Aspects of the disclosure combinable with any of the other aspects can include the following features. The imaging system includes a camera.

Aspects of the disclosure combinable with any of the other aspects can include the following features. The imaging system includes a microscope.

Certain aspects of the subject matter described here can be implemented as a method. A live emulsion of a live hydrocarbon sample and a water sample is flowed through a closed loop fluid flow system. The live hydrocarbon sample includes dissolved gases retrieved from a hydrocarbon-carrying reservoir. While flowing the live emulsion through the closed loop fluid flow system, a demulsifier sample is flowed through the closed loop fluid flow system. The demulsifier sample is capable of breakdown of the live emulsion. Flow of a portion of a mixture of the live emulsion and the demulsifier sample is isolated in a portion of the closed loop fluid flow system. Multiple images of the breakdown of the live emulsion over time are captured within the portion of the closed loop fluid flow system. An effectiveness of the demulsifier sample based, in part on the multiple images, is classified.

Aspects of the disclosure combinable with any of the other aspects can include the following features. To isolate flow of the portion of the mixture in the portion of the closed loop fluid flow system, the portion of the mixture is flowed into the portion of the closed loop fluid flow system, and a first valve upstream of and a second valve downstream of the portion of the closed loop fluid flow system are closed.

Aspects of the disclosure combinable with any of the other aspects can include the following features. With the portion of the mixture isolated in the portion of the closed loop fluid flow system, a remainder of the mixture is continued to flow through a remainder of the closed loop fluid flow portion.

Aspects of the disclosure combinable with any of the other aspects can include the following features. The remainder of the mixture is flowed through a capillary viscometer fluidically coupled in series with the remainder of the closed loop fluid flow system. Using the capillary viscometer, change in a viscosity of the live emulsion over time resulting from breakdown of the live emulsion due to the demulsifier sample is measured. The strength of the demulsifier is classified based, in part, on the change in the viscosity of the live emulsion over time.

Aspects of the disclosure combinable with any of the other aspects can include the following features. The demulsifier sample is a first demulsifier sample. The live emulsion is a first live emulsion. A second live emulsion of the live hydrocarbon sample and the water sample is flowed through the closed loop fluid flow system. While flowing the second live emulsion through the closed loop fluid flow system, a second demulsifier sample is flowed through the closed loop fluid flow system. The second demulsifier sample is capable of breakdown of the live emulsion. Flow of a portion of a mixture of the second live emulsion and the second demulsifier sample is isolated in a portion of the closed loop fluid flow system. Multiple images of the breakdown of the second live emulsion over time within the portion of the closed loop fluid flow system are captured.

Aspects of the disclosure combinable with any of the other aspects can include the following features. The effectiveness of the first demulsifier is further classified, based on the plurality of images of the breakdown of the second live emulsion over time.

Aspects of the disclosure combinable with any of the other aspects can include the following features. A concentration of the second demulsifier sample is different from a concentration of the first demulsifier sample.

Aspects of the disclosure combinable with any of the other aspects can include the following features. A temperature at which the second demulsifier sample and the second live emulsion are flowed is different from a temperature at which the first demulsifier sample and the first live emulsion are flowed.

Aspects of the disclosure combinable with any of the other aspects can include the following features. A pressure at which the second demulsifier sample and the second live emulsion are flowed is different from a pressure at which the first demulsifier sample and the first live emulsion are flowed.

Aspects of the disclosure combinable with any of the other aspects can include the following features. The live emulsion is formed by flowing the hydrocarbon sample and the water sample through the closed loop fluid flow system, and applying a shear force to the hydrocarbon sample and the water sample in the closed loop fluid flow system to form the live emulsion.

Certain aspects of the subject matter described here can be implemented as a method. Multiple live emulsions are formed. Each live emulsion is formed from a live hydrocarbon sample and a water sample. The live hydrocarbon sample includes dissolved gases retrieved from a hydrocarbon-carrying reservoir. For each live emulsion, the live emulsion is flowed through a closed loop fluid flow system. While flowing the live emulsion through the closed loop fluid flow system, a demulsifier sample is injected into the closed loop fluid flow system. The demulsifier sample is capable of breakdown of the live emulsion. Flow of a portion of a mixture of the live emulsion and the demulsifier sample in a portion of the closed loop fluid flow system is isolated. Multiple images of the breakdown of the live emulsion over time within the portion of the closed loop fluid flow system are captured. An effectiveness of the demulsifier sample is classified based, in part, on the multiple images.

Aspects of the disclosure combinable with any of the other aspects can include the following features. To form each live emulsion, a mixture of the hydrocarbon sample and the water sample are flowed through the closed loop fluid flow system until a viscosity of the mixture substantially stabilizes over time.

Certain aspects of the subject matter described here can be implemented as an apparatus. The apparatus includes a closed loop fluid flow system including an elongated tube arranged as a closed loop. The apparatus includes multiple containers coupled to the closed loop fluid flow system. The containers include a first container carrying live hydrocarbon comprising dissolved gases retrieved from a hydrocarbon-carrying reservoir, a second container carrying water, and a third container carrying a demulsifier configured to breakdown a live emulsion formed by the live hydrocarbon and the water. The apparatus includes a fluid flow system fluidically coupled to the closed loop fluid flow system and the multiple containers. The fluid flow system is configured to flow a live hydrocarbon sample from the first container, a water sample from the second container and a demulsifier sample from the third container through the closed loop fluid flow system. The apparatus includes an imaging system fluidically coupled to the closed loop fluid flow system. The imaging system is configured to capture images or video of the breakdown of the live emulsion formed by the live hydrocarbon sample and the water sample by the demulsifier sample.

Aspects of the disclosure combinable with any of the other aspects can include the following features. The fluid flow system includes a pump fluidically connected in series to the multiple containers.

Aspects of the disclosure combinable with any of the other aspects can include the following features. The apparatus includes a viewing cell within which a portion of the elongated tube is positioned. The viewing cell and the imaging system are spatially positioned such that the imaging system is configured to capture the images or the video when the live emulsion and the demulsifier sample reside in the portion of the elongated tube.

Aspects of the disclosure combinable with any of the other aspects can include the following features. The fluid flow system includes a first valve upstream of the viewing cell and a second valve downstream of the viewing cell. The first valve and the second valve are configured to isolate flow of a portion of a mixture of the live emulsion and the demulsifier in the portion of the elongated tube within the viewing cell.

Aspects of the disclosure combinable with any of the other aspects can include the following features. The imaging system includes a camera.

Aspects of the disclosure combinable with any of the other aspects can include the following features. The imaging system includes a microscope.

The details of one or more implementations of the subject matter described in this specification are set forth in the accompanying drawings and the description that follows. Other features, aspects, and advantages of the subject matter will become apparent from the description, the drawings, and the claims.

BRIEF DESCRIPTION OF THE DRAWINGS

FIG. 5 is a flowchart of an example of a process for classifying live hydrocarbon liquid-water emulsions using the apparatus of FIG. 4.

FIG. 7 is a plot comparing effectiveness of four demulsifiers.

Like reference numbers and designations in the various drawings indicate like elements.

DETAILED DESCRIPTION

Figure 1:
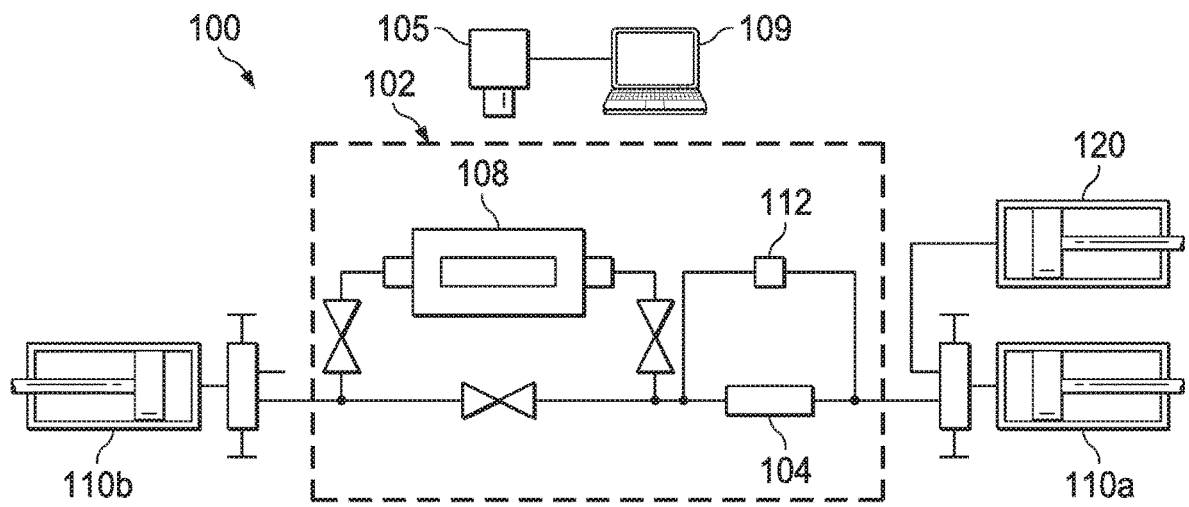
FIG. 1 is a schematic diagram of an apparatus for evaluating demulsifier effectiveness.

This disclosure describes methods and apparatuses to study the effect of demulsifiers on live emulsion samples.

In some implementations, an apparatus to implement the study includes a viscometer and a viewing cell connected in series and placed in a temperature-controlled environment. A live emulsion sample is introduced into the viewing cell and the viscometer. Different quantities of demulsifiers are added to the live emulsion sample to break the samples. The viscosity of the sample-demulsifier mixture is measured using the viscometer, and images of the mixture are captured through the viewing cell. An effect of the varying quantities of the demulsifier on the live emulsion sample are studied based on the viscosity measurements and using the images. For example, a decrease in viscosity combined with visual evidence of breakdown of the live emulsion indicates that a demulsifier is effective.

In some implementations, an apparatus to implement the study includes a closed loop flow system and the viewing cell, both of which are placed in a temperature-controlled environment. A live emulsion sample is introduced into the closed loop flow system and the viewing cell. Different quantities of demulsifiers are added to the live emulsion sample to break the sample. A quantity of the sample is statically held within the viewing cell. The separation of the live emulsion sample into the live hydrocarbon sample and water is imaged over time. An effect of the varying quantities on the live emulsion sample are studied based on results of the imaging over time. For example, a first demulsifier is considered more effective than a second demulsifier if the first demulsifier causes breakdown of the live emulsion sample faster than the second demulsifier.

Implementing the techniques described in this disclosure can provide objective and scientific observations about the effect of demulsifiers on breakdown of live emulsions as opposed to subjective results obtained from alternative techniques such as the bottle test. The techniques described in this disclosure test live samples under dynamic conditions rather than dead samples tested under static conditions. In addition, the sample is tested under the temperature and pressure at which the sample is retrieved from the subsurface reservoir rocks or a processing facility (for example, a temperatures ranging between 20 degrees Centigrade (° C.) and 150° C. and pressures ranging between 0 pounds per square inch area (psia) and 5000 psia), which are different from room temperature and atmospheric pressure. Consequently, the effects of the demulsifier on the sample as obtained by implementing the techniques described in this disclosure are more accurate and representative compared to techniques in which the sample is tested at room temperature or atmospheric pressure. The method avoids the artifacts of aging and exposure to air that can alter the properties of the crude oil and the live emulsion.

At the outset, an emulsion sample is collected from subsurface reservoir rocks or a processing facility. For example, the entrapped hydrocarbons can be produced through one or more production wellbores formed from the subsurface reservoir rocks to the surface processing facilities. A sample of the produced live emulsion can be obtained at a location at which properties of the subsurface reservoir rocks are known or can be determined, for example, at a pre-determined depth from the surface at which the temperature and pressure can be measured. Alternatively, the sample can be obtained from a trunkline carrying the live emulsions to the surface. In some implementations, the live emulsion with the live hydrocarbons obtained at the pre-determined depth, can be entrapped in a sampling container. The sampling container can maintain the live emulsion sample at the same conditions as the location from which the sample was obtained. The quantity of sample obtained can be sufficient to implement the techniques described later with reference to the following figures. Such a sampling container can include valves and tubes that connect the container to the flowline through which the fluids are produced. The container can additionally be connected to pressure gauges to monitor pressures of the fluids received in the sampling container and valves to control flow into or out of the container.

Dynamic Classification

FIG. 1 is a schematic diagram of an apparatus 100 for evaluating demulsifier effectiveness. The apparatus 100 includes a capillary viscometer 104 through which fluids, for example, a live emulsion sample formed with live hydrocarbon and water, a demulsifier sample, or any combination of them, can be flowed. Properties of the viscometer, for example, dimensions such as length, inner diameter, outer diameter, and material from which the viscometer is made, can be chosen to be suitable to implement the techniques described in this disclosure. For example, the viscometer can be made of stainless steel or similar material. In one example, the viscometer can have an outer diameter of 6.35 millimeters (mm), an inner diameter of 4.57 mm, a tube wall thickness of 0.89 mm and a length of 6,096 mm. As explained earlier, in other examples, the viscometer can be made of other materials (for example, heat conducting materials with large tensile strength) or have other dimensions or both.

A demulsifier is a chemical compound, for example, a mixture of chemicals and surfactants, that can breakdown the live emulsion. Breakdown of the live emulsion is a separation, over time, of the hydrocarbon liquid sample and the water sample from each other into separate phases. Live emulsion breakdown is characterized by the aggregation of bubbles in a mixture of the live emulsion and the demulsifier. Live emulsion texture (also known as bubble density) is a parameter for determining live emulsion strength and viscosity. Live emulsion texture is defined as bubble size per unit volume. Small bubble size or greater bubble density indicates high live emulsion strength compared to large bubble size or smaller bubble density which indicates low live emulsion strength.

The apparatus 100 can be used to test the live emulsion described earlier and to subsequently breakdown the live emulsion using a demulsifier. When the demulsifier breaks down the live emulsion, a viscosity of a mixture of the live emulsion and the demulsifier changes (for example, decreases) and bubbles form and propagate. The viscometer 104 can be implemented to measure change in a viscosity of the live emulsion over time resulting from a breakdown of the live emulsion by the demulsifier.

The viscometer 104 can include two pumps (for example, reciprocating pumps 110a and 110b) connected to the first end and the second end, respectively, of the viscometer 104. Each pump can be operated synchronously to flow the mixture of the live emulsion and the demulsifier through the viscometer 104 such that one pump applies a positive pressure to push the mixture through the section while the other pump applies an equal and opposite negative pressure to draw the mixture through the viscometer 104. After the mixture has flowed from substantially one end of the viscometer 104 to the other end, then the pressures of the two pumps are reversed to cause the mixture to flow through the viscometer 104 in the opposite direction. The viscometer 104 can be connected to a differential pressure sensor 112 that can measure the differential pressure across the viscometer 104 resulting from the fluid flow.

The apparatus 100 includes a syringe pump 120 fluidically coupled in parallel with the reciprocating pumps. The syringe pump 120 can be implemented to inject fluids (for example, demulsifiers) into the capillary viscometer 104. For example, a fluid to be injected can be flowed using the syringe pump 120 into a fluid line that couples the syringe pump 120 to one of the reciprocating pumps. Then, the reciprocating pumps can be operated in conjunction to flow the injected fluid through the capillary viscometer 104.

The apparatus 100 also includes an imaging system connected to the viscometer 104. The imaging system can include a viewing cell 108 and a camera 105 or a microscope (or both) spatially arranged relative to the viscometer 104 to capture images or video of the breakdown of the live emulsion caused by the demulsifier. In some implementations, the camera 105 (or a microscope or both) can be positioned such that the viewfinder of the camera 105 is directed at the viewing cell 108. The camera 105 can capture images or record video of the fluid flowing through the viewing cell 108. The camera 105 can be connected to a computer system 109 that includes a user interface (for example, a computer monitor) connected to one or more processors and a computer-readable medium, for example, a non-transitory computer-readable medium. The medium can store instructions executable by the one or more processors to perform some or all of the operations described in this disclosure. For example, the user interface can display the images or video captured by the camera 105. The computer system 109 can perform operations, for example, image processing operations on the captured images or video. An elongated tube connected to the viscometer 104 can be positioned within the viewing cell 108. The elongated tube can have the same inner diameter as the viscometer 104 and can have a transparent body through which the live emulsion flow and breakdown can be viewed or imaged or both. That is, only the length of the elongated tube which is positioned within the viewing cell 108 need be transparent.

In some implementations, the apparatus 100 can be positioned within a temperature-controlled housing 102, for example, an oven. By controlling the temperature within the housing 102, and by controlling the pressure with the pumps (110a and 110b), the techniques described in this disclosure can be implemented at temperatures and pressures that are substantially similar to the processing facilities or subsurface reservoir rock conditions at which the live emulsions are formed. For example, the housing 102 can be operated at a temperature that is within a plus-or-minus 5% variation from a temperature of the subsurface reservoir rock. The pumps 110a and 110b can be operated to apply a pressure that is within a plus-or-minus 5% variation from a pressure of the subsurface rock.

Figure 2:
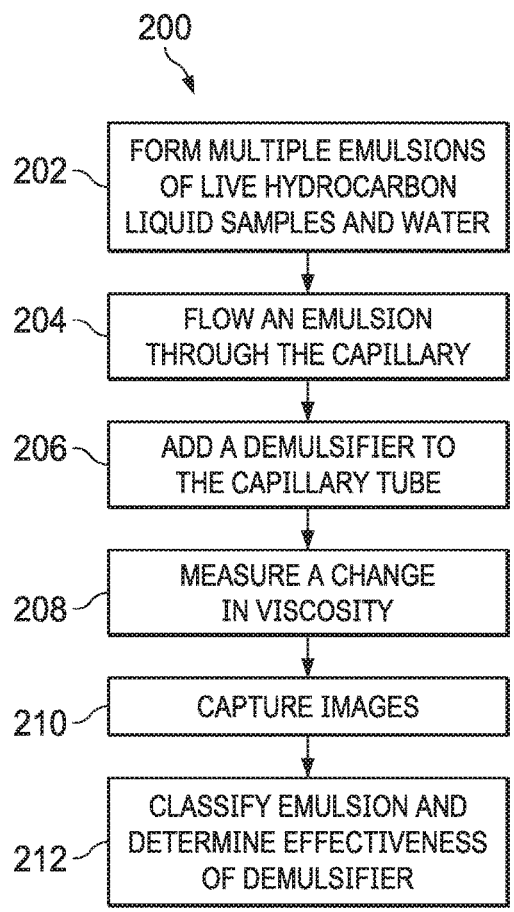
FIG. 2 is a flowchart of an example of a process for classifying live hydrocarbon liquid-water emulsions using the apparatus of FIG. 1.

FIG. 2 is a flowchart of an example of a process 200 for classifying liquid-water live emulsions formed from live hydrocarbons. At 202, multiple live emulsions of live hydrocarbons and water are formed. To do so, a mixture of a live hydrocarbon sample and a water sample can be injected into the viscometer 104, for example, using the syringe pump 120 or one of the pumps 110a or 110b. The mixture of the live hydrocarbon sample and the water sample can be sheared, for example, by flowing the mixture back and forth multiple times through the viscometer 104, to form the live emulsion. To do so, in some implementations, the two pumps 110a, 110b can be operated synchronously, as described earlier. In some implementations, the live emulsion can be formed separately, that is, outside the viscometer 104.

At 204, the live emulsion is flowed through the viscometer. In examples in which the live emulsion is formed within the capillary viscometer 104, the pumps can be operated to flow the live emulsion. In examples in which the live emulsion is formed outside the viscometer 104, the live emulsion can be injected into the capillary viscometer 104 using the syringe pump 120. In this manner, after forming the live emulsion, a pre-determined quantity of the live emulsion can be flowed through the viscometer 104. The pre-determined quantity of the live emulsion and those of other fluids to be injected into the viscometer 104 can be chosen based on factors including the inner volume of the viscometer 104. One or both of the pumps 110a, 110b can be operated to flow the live emulsion through the viscometer 104 at pre-determined pressures. The pressure in the system is set by the pump and can vary from atmospheric to the maximum allowable working pressure of the viscometer 104 and the viewing cell 108 (up to several thousand pounds per square inch).

At 206, a demulsifier is added to the viscometer. For example, after flowing the pre-determined quantity of the live emulsion into the viscometer 104, a pre-determined quantity of a demulsifier can be injected into the viscometer 104, for example, using the syringe pump 120, to mix with the live emulsion. The demulsifier can breakdown the live emulsion, that is, separate, the live hydrocarbon sample and the water sample. Examples of demulsifiers include those formulated with polymeric chains of one of ethylene oxides and polypropylene oxides of alcohol, ethoxylated phenols, ethoxylated alcohols and amines, ethoxylated resins, ethoxylated nonylphenols, polyhydric alcohols, or sulphonic acid salts. The concentration of the demulsifier can be determined based on the demulsifier type and its effectiveness in breaking down the live emulsion. For example, the demulsifier concentrations can range from less than 5 parts per million (ppm) by volume, which is approximately 1 gallon (gal) per 5,000 barrels (bbls) to more than 200 ppm (approximately 8 gal/1,000 bbls). For example, the quantity of the demulsifier can range between 10 ppm and 50 ppm. In general, the quantity of the demulsifier can be sufficient to diffuse the oil-water interface of the live emulsion but not greater than the critical aggregate micelle concentration. As described later, the separation of the hydrocarbon liquid sample-water live emulsion over time in response to adding the demulsifier is monitored.

At 208, a change in viscosity of the mixture of the live emulsion and the demulsifier is measured. For example, the viscometer 104 can be used to measure the viscosity of the mixture of the live emulsion and the demulsifier. To do so, the two pumps 110a, 110b are operated synchronously, as described earlier, causing the mixture of the live emulsion and the demulsifier to flow back and forth in the viscometer 104. As the demulsifier breaks down the live emulsion during the synchronous flow, the viscosity of the mixture and its rheology change over time. Most live emulsions are classified as non-Newtonian fluids whose apparent viscosity depends on shear rate ($\gamma$), which induces a shear stress ($\tau$) in the flowing fluid. Apparent viscosity ($\mu_{apparent}$) is determined according to Eqs. 1-3.

$$\mu_{apparent} = \frac{\tau}{\gamma} \quad \text{(Eq. 1)}$$

$$\tau = \frac{D \Delta P}{4L} \quad \text{(Eq. 2)}$$

$$\gamma = \frac{8V}{D} \quad \text{(Eq. 3)}$$

In Eqs. 2 and 3, D is the diameter of the viscometer 104, $\Delta P$ is the pressure drop across the viscometer 104 measured, for example, using the pressure sensor 112, L is the length of the viscometer, and V is the fluid flow velocity. To measure the viscosity at a time instant, the pressure drop across the viscometer 104 at a fixed shear rate in either direction is measured using the differential pressure sensor 112. The measurement is repeated at multiple time instants. The duration between two time instants can be sufficient for the viscosity to stabilize during that interval. By stabilizing of viscosity over time, it is meant that a rate of change of the viscosity over time is less than a threshold change. For example, when a slope of a plot of viscosity over time is close to zero (such as less than 1 or 2), then the viscosity is considered as having stabilized. Eqs. 1-3 can be solved, for example, using the computer system 109.

In some implementations, Eqs. 1-3 are applied to determine the viscosity at each time instant. In some implementations, the pressure drop can be measured multiple times between two time instants and a viscosity determined for each measured pressure drop. An average viscosity between two time instants can be determined. By measuring viscosity over time, a viscosity profile, that is, a plot of viscosity over time, can be developed for the mixture of the live emulsion and the demulsifier. As the demulsifier breaks down the live emulsion over time, the viscosity of the mixture will decrease. Once the live emulsion has broken down, the viscosity will remain substantially steady.

At 210, multiple images of the breakdown of the live emulsion over time are captured. The images can be static images or video. As the demulsifier breaks down a live emulsion, small bubbles begin to coalesce into larger bubbles in the mixture of the live emulsion and the demulsifier. The texture of the live emulsion changes as the bubble size and coalescence takes place. Live emulsion texture is a parameter used to determine live emulsion strength and viscosity. Live emulsion texture, also known as bubble density, is defined as bubble size per unit volume. There is an inverse relationship between bubble density and bubble size. The apparent viscosity of a live emulsion depends on the live emulsion texture. Smaller bubbles indicate higher apparent viscosity and vice versa.

Figure 3A:
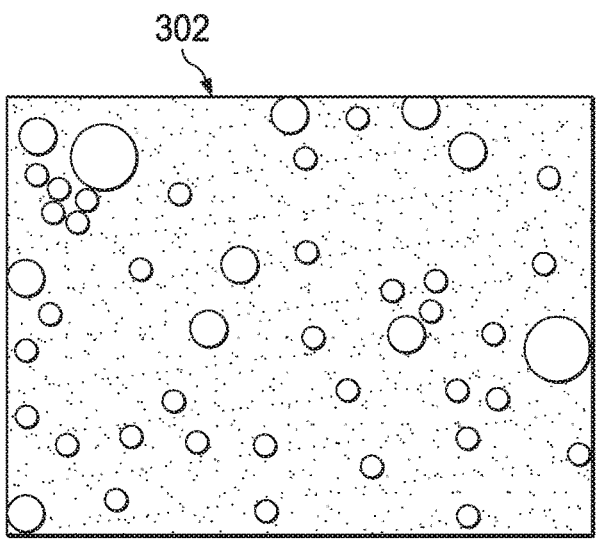
FIG. 3A is a schematic diagram representing a strong emulsion.

FIG. 3A is a schematic diagram 302 of a live emulsion. The schematic diagram 302 represents an image captured at a time instant before adding a demulsifier to a live emulsion. The bubbles are indicative of the tightness of the live emulsion. After adding the demulsifier, the images of the live emulsions are captured over time. In some implementations, multiple images of the breakdown can be captured over time. For example, an image can be captured each time a pressure drop is measured. Alternatively or in addition, an image can be captured each time an average viscosity is determined. The bubble size and bubble density in the images will change over time reflecting the breakdown of the live emulsion by the demulsifier. After a while, the breakdown reaches steady state following which the bubble size and bubble density in the images will remain substantially unchanged.

Figure 3B:
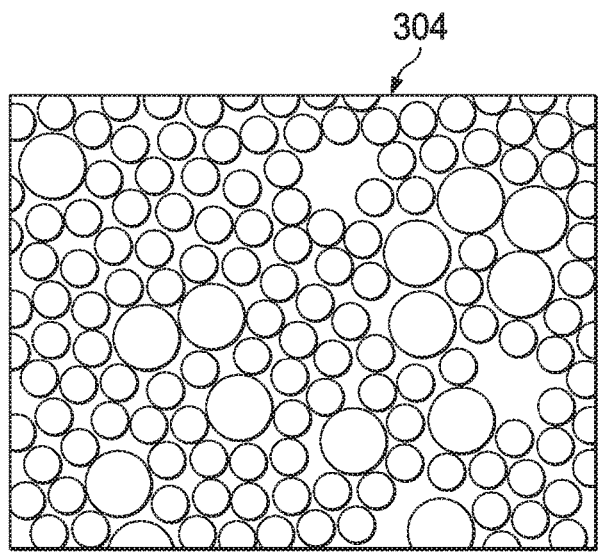
FIG. 3B is a schematic diagram representing a medium-strength emulsion.
Figure 3C:
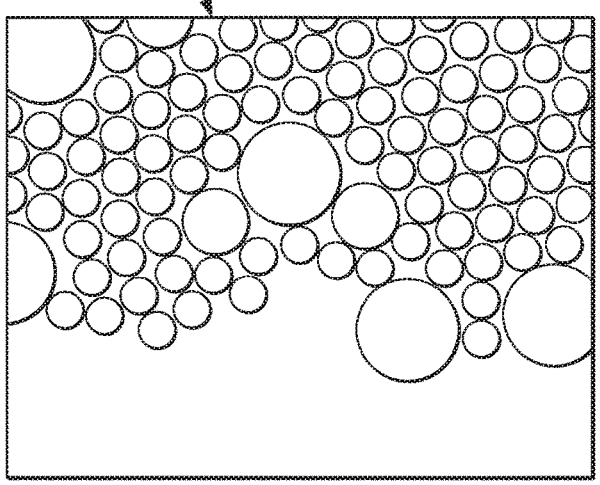
FIG. 3C is a schematic diagram representing a weak emulsion.

Back to FIG. 2, at 212, the live emulsion is classified. For example, the live emulsion can be classified as a strong live emulsion, a medium-strength live emulsion or a weak live emulsion based, in part, on bubble size and bubble density. The schematic diagram 302 (FIG. 3A) is represents a strong live emulsion. The schematic diagram 304 (FIG. 3B) represents a medium-strength live emulsion because the bubble size is greater than that of schematic diagram 302 and the bubble density is less than that of the schematic diagram 302. The schematic diagram 306 (FIG. 3C) represents a weak live emulsion because the bubble size is greater than that of the schematic diagram 304 and the bubble density is less than that of the schematic diagram 304.

In some implementations, the classification of the live emulsion based on the image can be performed manually or using computer-implemented software or both. For example, the computer software can receive, as input, a portion of the live emulsion image that includes bubbles and return, as output, a histogram showing a range of sizes of the bubbles in the image.

In some implementations, an effectiveness of the demulsifier to breakdown the live emulsion can also be classified based, in part, on the viscosity profile and the images. For example, if the viscosity profile shows a drop in viscosity over a short duration for a strong live emulsion whose images have small bubble size or large bubble density, then the demulsifier has a greater effectiveness. Conversely, if the viscosity profile shows a drop in viscosity over a comparatively long duration for a weak live emulsion whose images have a comparatively large bubble size or a comparatively low bubble density, then the demulsifier has a comparatively poorer effectiveness.

Static Classification

Figure 4:
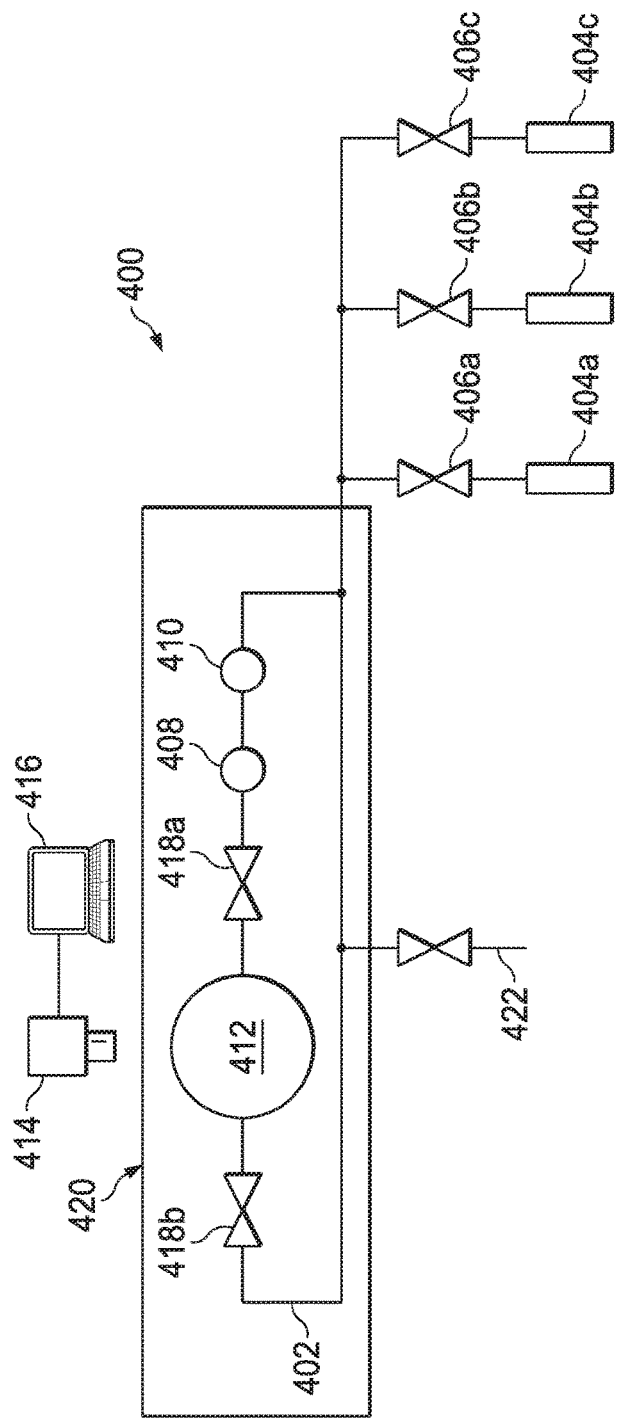
FIG. 4 is a schematic diagram of an apparatus for evaluating demulsifier effectiveness.

FIG. 4 is a schematic diagram of an apparatus 400 for evaluating demulsifier effectiveness. The apparatus 400 includes a closed loop fluid flow system 402 through which fluids, for example, a live hydrocarbon sample, water, an emulsion formed of the two, a demulsifier, or any combination of them, can be flowed. In some implementations, the closed loop fluid flow system 402 is an elongated tube, for example, a capillary tube similar to that used with the capillary viscometer 104 described earlier. The apparatus 400 includes multiple containers (for example, containers 404a, 404b, 404c) fluidically coupled to the closed loop fluid flow system 402. For example, each container can be fluidically coupled to the capillary tube to reside outside the closed loop and to inject fluid carried by the container into the closed loop. For example, container 404a, container 404b and container 404c can carry live hydrocarbon, water and demulsifier, respectively. The demulsifier can be similar to the demulsifier described earlier with reference to apparatus 100. In some implementations, the volume of the flow system 402 can be between 250 milliliters (ml) and 300 ml, for example, 260 ml.

In some implementations, a valve 406a, a valve 406b and a valve 406c can regulate flow of the fluid carried by the container 404a, the container 404b and the container 404c into the capillary tube. For example, each container can be fluidically coupled to a respective pump (not shown) to draw fluids from the container and to flow the drawn fluids into the closed loop flow system 402 when the corresponding valve is in an open state. Subsequently, the corresponding valve can be closed and remain closed to prevent fluid from the container from flowing into the closed loop fluid flow system 402 and vice versa. In some implementations, fluids from the containers injected into the closed loop fluid flow system 402 can be flowed through the system 402 by a fluid flow system 408. For example, the fluid flow system 408 can include a circulation pump fluidically coupled in-line with the capillary tube. One or more of the valves 406a, 406b or 406c can be placed in an open state, and the pump operated to draw pre-determined volumes of fluids from the respective containers into the capillary tube. Subsequently, the opened valves can be transitioned to a closed state, and the pump operated to flow fluids through the capillary tube.

In some implementations, an imaging system 414 can be fluidically coupled to the closed loop fluid flow system 402. For example, the imaging system 414 can include a viewing cell 412 and a camera 414 or a microscope (or both) spatially arranged relative to the viewing cell 412 to capture images or video of the breakdown of the live emulsion caused by the demulsifier. The viewing cell 412 can be partially or entirely transparent. In some implementations, the camera 414 (or a microscope or both) can be positioned such that the viewfinder of the camera 414 is directed at the viewing cell 412. The camera 414 can capture images or record video of the fluid residing in the viewing cell 12. As described later, breakdown of the live emulsion in the viewing cell 412 manifests as a separation of the live hydrocarbon and the water. The camera 414 can be positioned to image the separation. For example, as the live hydrocarbon and the water separate due to breakdown of the emulsion, the heavier of the two fluids can settle to the bottom of the viewing cell 412 and the lighter of the two fluids can rise to the top of the viewing cell 412. The camera 414 can be positioned relative to the viewing cell 412 to image and capture the separation of the two fluids.

The camera 414 can be connected to a computer system 416 that includes a user interface (for example, a computer monitor) connected to one or more processors and a computer-readable medium, for example, a non-transitory computer-readable medium. The medium can store instructions executable by the one or more processors to perform some or all of the operations described in this disclosure. For example, the user interface can display the images or video captured by the camera 414. The computer system 416 can perform operations, for example, image processing operations on the captured images or video.

In some implementations, a valve 418a and a valve 418b can be fluidically coupled to the closed loop fluid flow system 402 upstream and downstream, respectively, of the viewing cell 412. The two valves can isolate flow of a portion of fluid in the viewing cell 412. That is, the upstream valve 418a can be in an open state and the downstream valve 418b can be in a closed state to permit fluid flowing through the closed loop fluid flow system 402 to accumulate in the viewing cell 412. Once the viewing cell 412 has been filled to a pre-determined level, then both valves can be in a closed state, thereby isolating the fluid in the viewing cell 412 from the remainder of the fluid in the closed loop fluid flow system 402. In some implementations, the apparatus 400 can be positioned within a temperature-controlled housing 420, for example, an oven.

In some implementations, an emulsion-generating shear device 410 can be fluidically coupled to the closed loop fluid flow system 402. For example, the device 410 can receive a live hydrocarbon sample and a water sample, and apply shear to the two to form the emulsion. In some implementations, the emulsion is formed by applying shear with the device 410 and flowing the mixture through the flow system 402 to form the live emulsion. For example, the mixture can be flowed through the closed loop of the flow system 402, multiple times to form the live emulsion. The flow pressure of the mixture can vary from a time when the live hydrocarbon and the water are flowed to when the live emulsion is formed. In some implementations, a differential pressure sensor (not shown) can be fluidically coupled to the flow system 402 to measure the flow pressure of the mixture. When the differential pressure stabilizes over time, then it can be concluded that the live emulsion has formed. By stabilizing of pressure over time, it is meant that a rate of change of the pressure over time is less than a threshold change. For example, when a slope of a plot of pressure over time is close to zero (such as less than 1 or 2), then the pressure is considered as having stabilized.

The apparatus 400 can be implemented to characterize the effectiveness of demulsifiers in demulsification of oil-water emulsions. For example, a pre-determined volume of live hydrocarbons and water are drawn from their respective containers and injected into the closed loop fluid flow system 402. The pump 408 flows the pre-determined volumes either at room temperature or at a pre-determined temperature regulated using the housing 420. The device 410 applies shear to and mixes the live hydrocarbons and water to form a live emulsion. The device 410 can be operated at a shear rate that is similar to the shear rate experienced by the live hydrocarbons and water when flowed through a production tubing or flow line. Then, a pre-determined volume of demulsifier is drawn from its respective container and injected into the closed loop fluid flow system 402. The device 420 mixes the demulsifier with the emulsion causing a breakdown of the emulsion. The pump 408 flows a portion of the mixture into the viewing cell 412 at which time the two valves 418a and 418b are transitioned to a closed state to isolate the fluid in the viewing cell 412. The imaging system 414 is operated to image the breakdown of the emulsion over time in the viewing cell 412. The process can be repeated for different concentrations of demulsifier, and the results compared to determine a quantity of demulsifier that is effective for demulsification of a live emulsion. The process can also be repeated at different process conditions, for example, different concentrations of live hydrocarbon or water to form live emulsions, different types of demulsifiers, different temperatures or pressures, or any combination of them. After breakdown of the live emulsion has been imaged under one or one set of process conditions, the fluids in the closed loop fluid flow system 402 can be drained, for example, through the drain line 422, and new fluids under new process conditions can be introduced for further evaluation.

FIG. 5 is a flowchart of an example of a process 500 for classifying live hydrocarbon liquid-water emulsions using the apparatus of FIG. 4. At 502, multiple live emulsions of live hydrocarbons and water are formed. To do so, a mixture of a live hydrocarbon sample and a water sample are drawn into the closed loop fluid flow system 402, for example, using pumps fluidically coupled to the containers carrying the samples. The device 410 can shear the samples and the pump 408 can flow the sheared mixture through the flow system 402 until the emulsion is formed. Different types of live emulsions can be formed by varying the quantities of the live hydrocarbon and water.

At 504, the live emulsion is flowed through the closed loop fluid flow system 402, for example, the capillary tube. For example, the pump 408 can flow the live emulsion through the closed loop of the flow system 402. In some implementations, the process conditions under which the live emulsion is flowed through the flow system 402 can be controlled. For example, the housing 420 can be operated to apply a range of temperatures to the live emulsion. Alternatively or in addition, the pump 408 can be operated to apply a range of pressures to the live emulsion. The process conditions can be selected to match subsurface reservoir conditions where hydrocarbons with the live emulsions are found or the flowline conditions through which hydrocarbons with the live emulsions are flowed.

At 506, a demulsifier is added to the capillary tube. For example, after flowing the pre-determined quantity of the live emulsion through the flow system 402, a pre-determined quantity of a demulsifier can be drawn from its container and injected into the capillary tube. Flowing the live emulsion and the demulsifier in the capillary tube can cause the two fluids to mix, thereby initiating breakdown of the live emulsion. In some implementations, the device 410 can be operated to apply shear to the mixture to increase the speed of mixing and breakdown initiation. The types of demulsifiers and concentrations of the same can be similar to those described earlier with reference to FIG. 2.

At 508, a portion of a mixture of the live emulsion and the demulsifier is received in the viewing cell. For example, the pump 408 flows the mixture of the live emulsion and the demulsifier into the viewing cell 412 in which the mixture accumulates. The viewing cell 412 can have a volume in the order of milliliters (ml), for example, less than 100 ml. In some implementations, an entirety of the viewing cell 412 is filled with the mixture of the live emulsion and the demulsifier. In some implementations, a portion (for example, one-half and two-thirds) of the viewing cell 412 is filled with the mixture. The portion in the viewing cell 412 is isolated by closing the valves 418a and 418b. Once isolated, the portion in the viewing cell is static. That is, not additional force or pressure is applied on the portion in the viewing cell 412. In some implementations, the pump 408 and the device 410 can be turned off to not apply the additional force or pressure to the portion in the viewing cell 412.

Figure 6C:
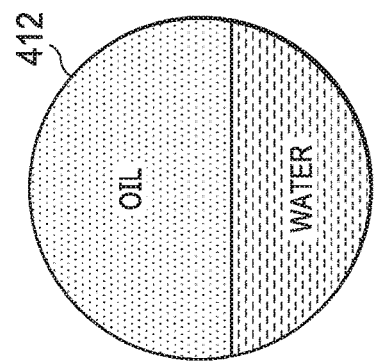
FIG. 6C is a schematic diagram of the live emulsion in the viewing cell after breakdown.
Figure 6B:
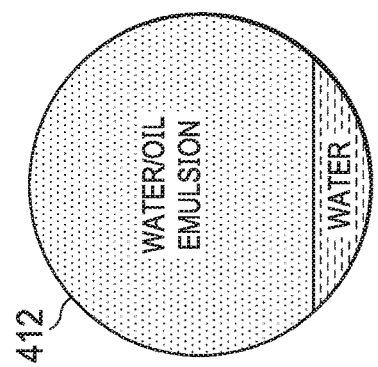
FIG. 6B is a schematic diagram of the live emulsion in the viewing cell during breakdown.
Figure 6A:
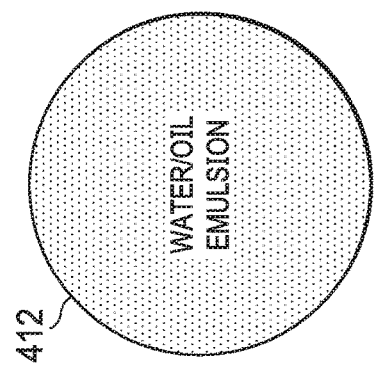
FIG. 6A is a schematic diagram of a live emulsion in a viewing cell before breakdown.

At 510, separation of live hydrocarbon and water over time is imaged in the viewing cell. Breakdown of the live emulsion due to the demulsifier results in separation of the live emulsion into live hydrocarbon and water. The immiscibility of the live hydrocarbon and water result in the heavier fluid settling to the bottom of the viewing cell 412 and the lighter fluid rising to the top of the viewing cell 412. Alternatively or in addition, the breakdown of the live emulsion due to the demulsifier results in the formation of bubbles. As breakdown continues over time, smaller bubbles coalesce to form larger bubbles indicating further separation. The camera 414 captures the breakdown, for example, the separation or the coalescing or both. For example, the camera 414 can capture video of the separation and coalescing over time. Alternatively or in addition, the camera 414 can periodically capture images of the separation and coalescing. The camera 414 can transfer the results of the imaging (that is, the videos or the images) to the computer system 416 for storage and further analysis FIG. 6A is a schematic diagram of a live emulsion in a viewing cell (for example, the viewing cell 412) before breakdown. FIG. 6B is a schematic diagram of the live emulsion in the viewing cell during breakdown. FIG. 6C is a schematic diagram of the live emulsion in the viewing cell after breakdown The diagrams schematically show the separation of the live emulsion into the live hydrocarbon and water. Before breakdown (FIG. 6A), the entire portion in the viewing cell 412 consists of the live emulsion. During breakdown (FIG. 6B), some water, having separated from the live emulsion, settles to the bottom of the viewing cell 412. After breakdown (FIG. 6C), all water in the live emulsion settles to the bottom while all live hydrocarbon in the live emulsion has risen to the top of the viewing cell 412.

Back at FIG. 5, at 512, the demulsifier is classified. For example, the demulsifier can be classified based on its effectiveness to breakdown and separate the live emulsion into the live hydrocarbon and water. To do so, the results of imaging the breakdown using the imaging system 414 can be examined to determine a time taken by a demulsifier to breakdown and separate the live emulsion. The examination can be performed manually. Alternatively, or in addition, the computer 419 can be programmed to perform the examination without user intervention. In one example, if the time taken by a first demulsifier to breakdown and separate a live emulsion under certain process conditions is less than the time by a second demulsifier to breakdown and separate the live emulsion under the same process conditions, then the first demulsifier has a greater effectiveness than the second demulsifier at those process conditions. In another example, if the time taken by a demulsifier to breakdown and separate a live emulsion under a first set of process conditions is less than the time taken by the same demulsifier to breakdown and separate the live emulsion under a second set of process conditions different from the first, then the demulsifier has a greater effectiveness at the first set of process conditions than the second. The process conditions can include a quantity of each of the live hydrocarbon and water used to form the live emulsion, process temperature or pressure (or both) or similar conditions. FIG. 7 is a plot 700 comparing effectiveness of four demulsifiers. The process conditions for the comparison are the following—temperature=120 degrees Fahrenheit (° F.), pressure =100 pounds per square inch (psi), demulsifier concentration=25 parts per million by volume, water cut=25%. The X-axis and Y-axis show separation time (in minutes) and water separation (in percentage) for each of the four demulsifiers.

The earlier portions of the disclosure described apparatuses and techniques to determine a strength of a live emulsion and of the effectiveness of a demulsifier to breakdown that live emulsion. The techniques can be repeated to determine the strength of multiple different live emulsions and of the effectiveness of either multiple, different demulsifiers or of the same demulsifier at different reservoir or processing conditions, for example, temperatures and pressures, or at different concentrations, or both. For example, in a first test, a pre-determined quantity of the live emulsion and a pre-determined quantity of the demulsifier can be tested as described earlier. In a second test, the same quantity of the live emulsion and a different quantity of the demulsifier (for example, one-half of or twice or three times) can be tested as described earlier. By repeating the test with different concentrations of the demulsifier, the effectiveness of the varying concentrations of the demulsifier on the breakdown of the live emulsion as well as strength of the live emulsion under the varying concentrations of the demulsifier can be determined.

In another example, in a first test, a pre-determined quantity of the live emulsion and a pre-determined quantity of the demulsifier can be tested at a first temperature as described earlier. In a second test, the same quantity of the live emulsion and the same quantity of the demulsifier can be tested at a second temperature different from the first temperature. By repeating the test at different temperatures, the effectiveness of the same quantity of the demulsifier at different temperatures on the breakdown of the live emulsion as well as strength of the live emulsion under the different temperatures can be determined.

In a further example, in a first test, a pre-determined quantity of the live emulsion and a pre-determined quantity of the demulsifier can be tested at a first pressure as described earlier. In a second test, the same quantity of the live emulsion and the same quantity of the demulsifier can be tested at a second pressure different from the first pressure. By repeating the test at different pressures, the effectiveness of the same quantity of the demulsifier at different pressures on the breakdown of the live emulsion as well as strength of the live emulsion under the different pressures can be determined. Similar tests can be performed by varying more than one test condition, for example, type of demulsifier, concentration of emulsifier, flow temperature, and flow pressure. Similar tests can also be performed by varying the initial concentration of the hydrocarbon liquid sample or the water sample (or both), or by varying the aging time to form different types of live emulsions to be tested. The output of the tests can be compiled to produce reference material (for example, tables, spreadsheets, or the like) that identify the conditions under which the live emulsions were formed, the information directed to the demulsifiers that were used to test the live emulsions and the process conditions (that is, temperatures, pressures) under which the tests were performed.

As described earlier, the apparatus 100 (FIG. 1) can be implemented to perform dynamic operations and the apparatus 400 (FIG. 4) can be implemented to perform static operations, both to evaluate the effectiveness of demulsifiers and strength of live emulsions. Components of the two apparatuses can be interchangeably used. For example, components used in the apparatus 100 can be similar or identical to those used in the apparatus 400 permitting the interchangeable use.

In some implementations, an apparatus that combines features of the apparatus 100 (FIG. 1) and the apparatus 400 (FIG. 4) can be constructed to perform the dynamic and static operations simultaneously. To do so, components described earlier with reference to each apparatus can be combined or re-purposed. For example, the sample carrying containers 404a, 404b, 404c of the apparatus 400 (FIG. 4) can be fluidically coupled to the synchronous pumps 110a, 110b of the apparatus 100 (FIG. 1) to allow pre-determined quantities of each fluid drawn from each of the containers 404a, 404b, 404c to be injected into the capillary viscometer 104. In addition, the portion of the closed loop fluid flow system 402 in which the portion of the mixture of the live emulsion and the demulsifier is isolated (that is, the viewing cell 412 with the upstream and downstream valves 418a, 418b) can be fluidically coupled in parallel to the capillary viscometer 104. In such an arrangement, the combined apparatus can be operated such that the change in the viscosity of a first portion of the mixture of the live emulsion and the demulsifier can be viewed in the viewing cell 108 (FIG. 1) at the same time that the separation of a second portion of the mixture of the live emulsion and the demulsifier is viewed in the viewing cell 412 (FIG. 4). Alternatively or in addition, the combined apparatus can also be operated to perform either the dynamic operations or the static operations independently. With such an arrangement, the effectiveness of the demulsifiers and the strength of the emulsion can be determined based on the change in the viscosity of and the bubble densities of images of the mixture of the live emulsion and demulsifier, as well as the time for separation of the live emulsion into the live hydrocarbon and water.

In some implementations, the operations described in this disclosure, for example, the control of any component of any apparatus or the analysis of the information captured by the information systems, can be performed by a controller operatively coupled to the apparatus, particularly, to each component of the apparatus. The controller can be implemented as a computer system including one or more processors and a computer-readable medium storing instructions executable by the one or more processors to perform the operations in this disclosure. In some implementations, the controller can be configured to perform multiple operations in any sequence, for example, in parallel or in series. For example, the controller can be programmed to implement an automated sequence of operations to classify multiple, different live emulsions or multiple, different emulsifiers or combinations of them. The controller can select pre-determined, different concentrations of live hydrocarbons and water to form multiple, different live emulsions. The controller can apply multiple, different process conditions to the live emulsions. The controller can select pre-determined, different types or concentrations (or both) of demulsifiers to mix with the live emulsions. The controller can operate the imaging systems to image the breakdown of the live emulsions, store the imaging information and perform classification operations. In particular, the controller can perform the described operations without user intervention.

Determining live emulsion strength and the effectiveness of demulsifiers at different conditions to breakdown live emulsions can allow controlling operations such as hydrocarbon processing operations implemented as GOSPs. For example, live emulsions in produced hydrocarbons can be broken down by adding pre-determined quantities of demulsifiers at known process conditions (that is, temperatures, pressures) to effectively break down the live emulsions. In particular, the reference material can be used to identify the optimal demulsifier and the optimal process conditions to breakdown different types of live emulsions in the produced hydrocarbons.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

The invention claimed is:

1. A method comprising:

flowing a live emulsion of a live hydrocarbon sample and a water sample through a closed loop fluid flow system, wherein the live hydrocarbon sample comprises dissolved gases retrieved from a hydrocarbon-carrying reservoir;

while flowing the live emulsion through the closed loop fluid flow system, flowing a demulsifier sample through the closed loop fluid flow system, wherein the demulsifier sample is capable of breakdown of the live emulsion;

isolating flow of a portion of a mixture of the live emulsion and the demulsifier sample in a portion of the closed loop fluid flow system;

capturing a plurality of images of the breakdown of the live emulsion over time within the portion of the closed loop fluid flow system; and classifying an effectiveness of the demulsifier sample based, in part, on the plurality of images.

2. The method of claim 1, wherein isolating flow of the portion of the mixture in the portion of the closed loop fluid flow system comprises:

flowing the portion of the mixture into the portion of the closed loop fluid flow system; and closing a first valve upstream of and a second valve downstream of the portion of the closed loop fluid flow system.

3. The method of claim 1, further comprising, with the portion of the mixture isolated in the portion of the closed loop fluid flow system, continuing to flow a remainder of the mixture through a remainder of the closed loop fluid flow system.

4. The method of claim 3, further comprising:

flowing the remainder of the mixture through a capillary viscometer fluidically coupled in series with the remainder of the closed loop fluid flow system; and measuring, using the capillary viscometer, change in a viscosity of the live emulsion over time resulting from breakdown of the live emulsion due to the demulsifier sample, wherein the strength of the demulsifier is classified based, in part, on the change in the viscosity of the live emulsion over time.

5. The method of claim 1, wherein the demulsifier sample is a first demulsifier sample and the live emulsion is a first live emulsion, wherein the method further comprises:
flowing a second live emulsion of the live hydrocarbon sample and the water sample through the closed loop fluid flow system;
while flowing the second live emulsion through the closed loop fluid flow system, flowing a second demulsifier sample through the closed loop fluid flow system, wherein the second demulsifier sample is capable of breakdown of the live emulsion;
isolating flow of a portion of a mixture of the second live emulsion and second the demulsifier sample in a portion of the closed loop fluid flow system; and
capturing a plurality of images of the breakdown of the second live emulsion over time within the portion of the closed loop fluid flow system.

6. The method of claim 5, wherein the effectiveness of the first demulsifier is further classified, in part, based on the plurality of images of the breakdown of the second live emulsion over time.

7. The method of claim 5, wherein a concentration of the second demulsifier sample is different from a concentration of the first demulsifier sample.

8. The method of claim 5, wherein a temperature at which the second demulsifier sample and the second live emulsion are flowed is different from a temperature at which the first demulsifier sample and the first live emulsion are flowed.

9. The method of claim 5, wherein a pressure at which the second demulsifier sample and the second live emulsion are flowed is different from a pressure at which the first demulsifier sample and the first live emulsion are flowed.

10. The method of claim 1, further comprising forming the live emulsion by:
flowing the hydrocarbon sample and the water sample through the closed loop fluid flow system; and
applying a shear force to the hydrocarbon sample and the water sample in the closed loop fluid flow system to form the live emulsion.

11. A method comprising:
forming a plurality of live emulsions, each live emulsion formed from a live hydrocarbon sample and a water sample, wherein the live hydrocarbon sample comprises dissolved gases retrieved from a hydrocarbon-carrying reservoir;
for each live emulsion:
flowing the live emulsion through a closed loop fluid flow system,
while flowing the live emulsion through the closed loop fluid flow system, injecting a demulsifier sample into the closed loop fluid flow system, wherein the demulsifier sample is capable of breakdown of the live emulsion;
isolating flow of a portion of a mixture of the live emulsion and the demulsifier sample in a portion of the closed loop fluid flow system;
capturing a plurality of images of the breakdown of the live emulsion over time within the portion of the closed loop fluid flow system; and
classifying an effectiveness of the demulsifier sample based, in part, on the plurality of images.

12. The method of claim 11, wherein forming the plurality of live emulsions comprises, for each live emulsion, flowing a mixture of the hydrocarbon sample and the water sample through the closed loop fluid flow system until a viscosity of the mixture substantially stabilizes over time.

13. An apparatus comprising:
a closed loop fluid flow system comprising an elongated tube arranged as a closed loop;
a plurality of containers fluidically coupled to the closed loop fluid flow system comprising:
a first container carrying live hydrocarbon comprising dissolved gases retrieved from a hydrocarbon-carrying reservoir,
a second container carrying water, and
a third container carrying a demulsifier configured to breakdown a live emulsion formed by the live hydrocarbon and the water;
a fluid flow system fluidically coupled to the closed loop fluid flow system and the plurality of containers, the fluid flow system configured to flow a live hydrocarbon sample from the first container, a water sample from the second container and a demulsifier sample from the third container through the closed loop fluid flow system; and
an imaging system fluidically coupled to the closed loop fluid flow system, the imaging system configured to capture images or video of the breakdown of the live emulsion formed by the live hydrocarbon sample and the water sample by the demulsifier sample.

14. The apparatus of claim 13, wherein the fluid flow system comprises a pump fluidically connected in series to the plurality of containers.

15. The apparatus of claim 13, further comprising a viewing cell within which a portion of the elongated tube is positioned, the viewing cell and the imaging system spatially positioned such that the imaging system is configured to capture the images or the video when the live emulsion and the demulsifier sample reside in the portion of the elongated tube.

16. The apparatus of claim 13, wherein the imaging system comprises a camera.

17. The apparatus of claim 13, wherein the imaging system comprises a microscope.

18. An apparatus comprising:
a closed loop fluid flow system comprising an elongated tube arranged as a closed loop;
a plurality of containers fluidically coupled to the closed loop fluid flow system comprising:
a first container carrying live hydrocarbon comprising dissolved gases retrieved from a hydrocarbon-carrying reservoir,
a second container carrying water, and
a third container carrying a demulsifier configured to breakdown a live emulsion formed by the live hydrocarbon and the water;
a fluid flow system fluidically coupled to the closed loop fluid flow system and the plurality of containers, the fluid flow system configured to flow a live hydrocarbon sample from the first container, a water sample from the second container and a demulsifier sample from the third container through the closed loop fluid flow system, wherein the fluid flow system comprises:
a first valve upstream of the viewing cell; and
a second valve downstream of the viewing cell, the first valve and the second valve configured to isolate flow of a portion of a mixture of the live emulsion and the demulsifier in the portion of the elongated tube within the viewing cell; and
an imaging system fluidically coupled to the closed loop fluid flow system, the imaging system configured to capture images or video of the breakdown of the live emulsion formed by the live hydrocarbon sample and the water sample by the demulsifier sample.

\* \* \* \* \*